(12) United States Patent
Day et al.

(10) Patent No.: US 7,977,107 B2
(45) Date of Patent: *Jul. 12, 2011

(54) ORAL DETECTION TEST FOR CANNABINOID USE

(75) Inventors: David Day, Sandy, UT (US); David J. Kuntz, Salt Lake City, UT (US); Michael S. Feldman, Salt Lake City, UT (US)

(73) Assignee: LabOne, Inc., Lenexa, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/896,792

(22) Filed: Oct. 1, 2010

(65) Prior Publication Data

US 2011/0020945 A1 Jan. 27, 2011

Related U.S. Application Data

(63) Continuation of application No. 12/270,782, filed on Nov. 13, 2008, now Pat. No. 7,816,143, which is a continuation of application No. 10/980,372, filed on Nov. 3, 2004, now Pat. No. 7,465,586.

(51) Int. Cl.
*G01N 33/94* (2006.01)
*B01D 59/44* (2006.01)

(52) U.S. Cl. ............ 436/93; 436/63; 436/161; 436/173; 436/901; 250/281; 250/282

(58) Field of Classification Search .................. 436/63, 436/161, 173, 169, 93, 901; 210/656; 250/281, 250/282, 283

See application file for complete search history.

(56) References Cited

U.S. PATENT DOCUMENTS

| | | | |
|---|---|---|---|
| 4,921,788 A | 5/1990 | Deutsch | |
| 5,036,014 A | 7/1991 | Elsohly et al. | |
| 5,264,373 A | 11/1993 | Wang et al. | |
| 5,292,899 A | 3/1994 | Tius et al. | |
| 5,302,703 A | 4/1994 | Buechler et al. | |
| 5,324,642 A | 6/1994 | Baumgartner | |
| 5,325,708 A | 7/1994 | De Simon | |
| 5,466,579 A | 11/1995 | Baumgartner | |
| 5,532,131 A | 7/1996 | Lewis | |
| 5,595,653 A | 1/1997 | Good et al. | |
| 5,817,766 A | 10/1998 | Hui et al. | |
| 6,022,693 A | 2/2000 | Baumgartner | |
| 6,063,637 A | 5/2000 | Arnold et al. | |
| 6,248,598 B1 | 6/2001 | Bogema | |
| 6,309,827 B1 | 10/2001 | Goldstein et al. | |
| 6,350,582 B1 | 2/2002 | Baumgartner | |
| 6,582,924 B1 | 6/2003 | Baumgartner | |
| 6,686,209 B2 | 2/2004 | Wang et al. | |
| 6,702,988 B1 | 3/2004 | Sagona et al. | |
| 7,465,586 B2 | 12/2008 | Day et al. | |
| 7,816,143 B2 * | 10/2010 | Day et al. | ......... 436/93 |
| 2002/0115089 A1 | 8/2002 | Goldstein et al. | |
| 2002/0142484 A1 | 10/2002 | Wang et al. | |

OTHER PUBLICATIONS

Package Insert for the AMP/MAMP/COC/OPI/THC/PCP Test for Oral Fluids, "Oral Fluid Drug Screen Device", Oct. 4, 2003, available at www.testcountry.com/iScreenOralInsert.pdf.*
Brandt, et al, J Planar Chromatography Modern TLC, (1997), 10(5):348-352 (abstract).
Chiarotti, et al, Forensic Sci Int, (2000), 114(1):1-6.
Cone, et al, J Anal Toxicol, (1987), 11(3):89-96 (abstract only).
Cone, et al, J Anal Toxicol, (2002), 26(8):541-546 (abstract only).
Gustafson, et al, J Chromatography B, (2003), 798:145-154.
Gustafson, et al, Clin Chem, (2003), 49(7):1114-1124.
Gustafson, et al, J Anal Toxicol, (2004), 28(3):160-167.
Kintz, et al, J Forensic Sci, (1995), 40(4):619-622 (abstract only).
Kintz, et al, www.icadts.org/proceedings/show.php?paper=2000-167.pdf, 2000.
Liang, et al, (2000), available at www.w.se/trat_sau/2000/Poster10.pdf.
Lindgren, et al, Psychopharmacology (Berl), (1981), 74(3):208-212.
Lyons, et al, J Anal Toxicol, (2001), 25(5):289-303 (abstract only).
Niedbala, et al, J Anal Toxicol, (2001), 25(5):289-303 (abstract only).
Notice of Allowance dated Aug. 12, 2008 in U.S. Appl. No. 10/980,372.
Peat, paper Mar. 27, 2000, available at http://www.4intercept.com/clinicals/test_results.html.
Perez-Reyes, et al, Clin Pharmacol Ther, (1983), 34(1):36-41 (abstract only).
Schramm, et al, J Anal Toxicol, (1992), 16(1):1-9.
Steinmeyer et al, J Chromatgraphy B, (2002), 772:239-248.
Stout, et al, J Anal Toxicol, (2001), 25(7):550-554.
US Notice of Allowance dated Jun. 16, 2010 in U.S. Appl. No. 12/270,782.
US Office Action dated Sep. 19, 2006 in U.S. Appl. No. 10/980,372.
US Office Action dated Oct. 30, 2007 in U.S. Appl. No. 10/980,372.
US Office Action dated Feb. 22, 2010 in related U.S. Appl. No. 12/270,782.
US Office Action dated Apr. 30, 2009 in U.S. Appl. No. 12/270,782.
Wall et al, J Clin Pharmacol, (1981), 21(8-9 Suppl):1785-189S (abstract only).
Wall, et al, Clin Pharmacol Ther, (1983), 34(3):352-363 (abstract only).

* cited by examiner

*Primary Examiner* — Maureen M Wallenhorst
(74) *Attorney, Agent, or Firm* — Foley & Lardner LLP

(57) ABSTRACT

A method for confirming the active intake of marijuana and its active component $\Delta^9$-tetrahydrocannabinol ("$\Delta^9$-THC") by detecting the amount of 11-nor-$\Delta^9$-THC carboxylic acid ("THCA") in oral fluid at the picogram per milliliter (pg/ml) level using chromatography/mass spectrometry/mass spectrometry ("GC/MS/MS").

14 Claims, 2 Drawing Sheets

Linearity of THCA from Oral Fluid by GC/MS/MS**

% Recovery of THCA from Oral Fluid**

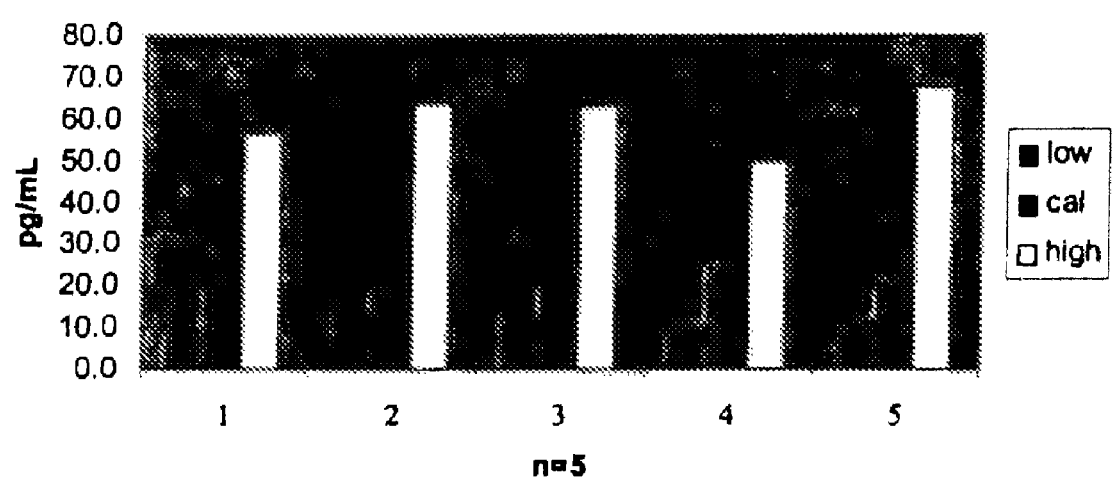

ORAL DETECTION TEST FOR CANNABINOID USE

CROSS-REFERENCE TO RELATED APPLICATIONS

This application is a continuation of U.S. application Ser. No. 12/270,782, filed Nov. 13, 2008, now issued as U.S. Pat. No. 7,816,143, which is a continuation of U.S. application Ser. No. 10/980,372, filed Nov. 3, 2004, issued as U.S. Pat. No. 7,465,586, each of which is hereby incorporated by reference in its entirety.

STATEMENT REGARDING FEDERALLY SPONSORED RESEARCH OR DEVELOPMENT

Not applicable.

BACKGROUND OF THE INVENTION

1. Field of the Invention

The field of the present invention relates to the detection of controlled substances, and in particular to the detection of a metabolite of $\Delta^9$-tetrahydrocannabinol ("$\Delta^9$-THC"). More specifically, the invention relates to the detection of 11-nor-$\Delta^9$-THC carboxylic acid ("THCA") in the oral fluid at the picogram per milliliter (pg/ml) level using mass spectrometry, such as gas chromatography/mass spectrometry/mass spectrometry ("GC/MS/MS") to screen and/or confirm active cannabinoid use in a test subject.

2. Description of Related Art

Marijuana, a known psychoactive drug, is derived from plants of the hemp family that produce significant amounts of cannabinoids. In particular, the most important cannabinoid is $\Delta^9$-THC, which is the major physiologically active constituent of marijuana. $\Delta^9$-THC is a controlled substance because it has both sedative and depressant-like effects on the cardiovascular and central nervous systems, as opposed to cannabidiol, a non-psychoactive constituent of marijuana. Through smoking marijuana, $\Delta^9$-THC is rapidly absorbed from the lungs into the blood stream and metabolized by the liver to a series of polar metabolites with THCA as the primary metabolite. More specifically, microsomal hydroxylation allylic to the $\Delta^9$-THC double bond occurs to form 11-OH-THC. Following this, non-microsomal oxidation to THCA occurs via alcohol dehydrogenase.

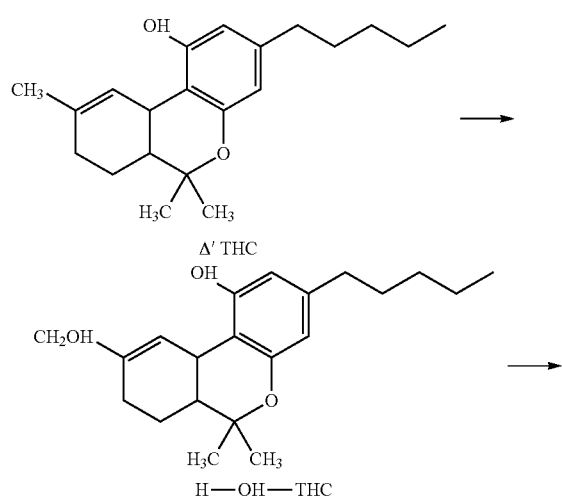

-continued

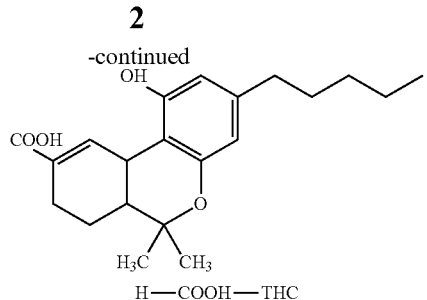

H—COOH—THC

The carboxylated compound is then conjugated to the glucuronide metabolite. The glucuronide conjugate is excreted as the major urine metabolite along with about 18 nonconjugated metabolites. The enzymes responsible for formation of THCA and THCA-glucuronide are not known to exist in the oral cavity.

Due to the common abuse of cannabinoids, there is a growing need for non-invasive and rapid tests to detect the presence of these controlled drugs in biological specimens. Currently, the presence of $\Delta^9$-THC in biological samples, such as urine, can be detected by a number of techniques such as thin layer chromatography ("TLC"), gas chromatography/mass spectrometry ("GC/MS"), GC/MS/MS, radioimmunoassay ("RIA"), or enzyme immunoassay ("EIA"). The established federal guidelines for initial screening cutoffs of $\Delta^9$-THC in urine have been set at a level of 50 ng/ml. In addition, the metabolite THCA has been detected in urine. See, e.g., Wang et al, U.S. Pat. No. 5,264,373, col. 1, lines 36-37; Gustafson et al., *Urinary Pharmacokinetics of 11-Nor-9-carboxy-$\Delta^9$-tetrahydrocannabinol after Controlled Oral $\Delta^9$-Tetrahydrocannabinol Administration*, J. Anal. Toxicol., Vol. 28, No. 3, at pp. 160-67 (April 2004) (limit of quantitation of 2.5 ng/ml); Lyons et al., *A Comparison of Roche Kinetic Interaction of Microparticles in Solution (KIMS) Assay for Cannabinoids, and GC-MS Analysis for 11-nor-carboxy-delta9-tetrahydrocannabinol*, J. Anal. Toxicol., Vol. 25, No. 7, at pp. 559-64 (October 2001) (15 ng/ml cutoff); Chiarotta et al., *Analysis of 11-nor-9-carboxy-delta(9)-tetrahydrocannabinol in biological samples by gas chromatography tandem mass spectrometry (GC/MS-MS)*, Forensic Sci. Int., Vol. 114, No. 1, at pp. 1-6 (October 2000) (urine sample spiked with THCA reported over 5 to 50 ng/ml range); Stout et al., *Solid-phase extraction and GC-MS analysis of THC-COOH method optimized for a high-throughput forensic drug-testing laboratory*, J, Anal. Toxicol., Vol. 25, No. 7, at pp. 550-54 (October 2001).

The presence of THCA has also been detected in hair. See, e.g., Baptista et al., Hair analysis for delta(9)-THC, delta(9)-THC-COOH, CSN and CBD, by GC/MS-EI: Comparison with GC/MS-NCI for delta(9)-THC-COOH, Forensic Sci. Int., Vol. 128, at pp. 68-78 (August 2002); Kintz et al., Testing human hair for *cannabis*. II: Identification of THC-COOH by GC-MS-NCI as a unique proof, J. Forensic Sci., Vol. 40, No. 4, at pp. 619-22 (July 1995) (0.02-0.39 ng/mg of THCA).

In recent years, there have been many reports concerning the use of oral fluid for drug monitoring for marijuana use. Oral fluid offers some advantages over other types of specimens. For example, oral fluid is readily accessible and its collection is perceived as less invasive than urine specimen collection. Thus, oral fluid requires less privacy intrusion than collection of urine. Further, oral fluid collections can easily be observed, and therefore, the specimen is less susceptible to adulteration or substitution by the donor. While testing for the presence of the parent compound $\Delta^9$-THC has been performed with oral fluid, there appears to be only a single report of the detection of marijuana metabolites in oral fluids. In 1992, a review paper by Schramm purported to identify THCA, 11-hydroxy-THC, cannabidiol, together with $\Delta^9$-THC in a single saliva specimen after smoking marijuana using HPLC and mass spectrometry, but the methodology was not otherwise reported. See Schramm et al., *Drugs of Abuse in Saliva: A Review*, J. Anal. Toxicol, Vol. 16, No. 1, at pp 1-9 (1992). According to Schramm, the presence of the THC and its metabolites was not the result of transfer from the blood because radiolabeled $\Delta^9$-THC administered by intravenous injection could not be detected in saliva. Id. (citing R. L. Hawks, *The Constituents of Cannabis and the Disposition and Metabolism of Cannabinoids*, Natl. Inst. Drug Abuse Res. Monog. Ser. 42: 125-37 (1982)); See also U.S. Pat. No. 6,309,827 to Goldstein et al. (example 8) (discussing how $\Delta^9$-THC and its metabolites appear to be sequestered in the buccal cavity during smoking rather than passing from the blood to the oral fluid). Thus, Schramm theorized that the $\Delta^9$-THC metabolites purportedly detected in the mouth came directly from the marijuana smoke or metabolism in the mouth such that detection of metabolites in saliva was limited to indication of recent use. However, the published studies performed to date have not confirmed this theory. The conclusion of the Schramm paper—that these metabolites, accumulated in the oral fluid from smoked marijuana by metabolism in the mouth—is not supported by the current data regarding the metabolism of THC. THCA and THCA-glucuronide are liver metabolites, and are not known to be formed in the oral cavity. See Watanabe K, et al., *A cytochrome P450 isozyme having aldehyde oxygenase activity plays a major role in metabolizing cannabinoids by mouse hepatic microsomes*, Biochem Pharmacol., Vol. 46 No. 3, at pp. 405-11 (August 1993).

Further, subsequent attempts by researchers to detect THCA in the oral fluid were unsuccessful when more sophisticated detection equipment was used than that in Schramm. For example, Huestis and Cone found no evidence by GC-MS (detection limit 0.5 ng/ml) of 11-hydroxy-THC or THCA over a period of seven days following smoked marijuana. See M. A Huestis and E. J. Cone, *Alternative Testing Matrices*, in DRUG ABUSE HANDBOOK, S. Karch, Ed., CRC Press, Boca Raton, Fla., at pp. 799-857 (1998). Further, Peat reported that THCA could not be detected in the mucosal transudate even when the detection limit was as low as 0.1 ng/ml using a GC/MS/MS assay, See Peat, *A Brief Introduction to Oral Fluid Drug Testing* (Mar. 27, 2000), available at http://www.4intercept.com/clinicals/brief_intro.html. Researchers theorized that the THCA was so strongly bound to plasma proteins that the compound did not diffuse into the oral cavity. See Kintz et al., *Pharmacological Criteria to Use Alternative Specimens for DUI Controls* (2000) available at www.vv.se/traf_sak/t2000/804.pdf; Kintz et al., *Detection of cannabis in oral fluid (saliva) and forehead wipes (sweat) from impaired drivers*, J. Anal. Toxicol., Vol. 24, No. 7, at pp. 557-61 (October 2000).

Researchers continue with attempts to develop assays to detect the presence of THCA in the oral fluid in the ng/ml range. For example, Liang and colleagues have attempted to develop a rapid instrumented fluorescence immunoassay for the detection and quantification of tetrahydrocannibanols in oral fluids using lower detection limits for $\Delta^9$-THC and THCA of 1.5 ng/ml and 5.5 ng/ml, respectively. These researchers, however, "spiked" pooled saliva from volunteers to provide the appropriate concentration of drug for testing. See Liang et al, *A Rapid Instrumented Fluorescence Immunoassay for the Detection of Tetrahydrocannibanols* (available at www.w.se/traf_sak/t2000/poster10.pdf). Similarly, U.S. Pat. No. 6,509,827 to Goldstein et al., has reported "spiking" oral collection devices with various concentrations of metabolites. Table 5 of the patent shows THCA concentrations around 10 ng/ml. The cutoff for oral fluid detection $\Delta^9$-THC and the metabolites using EIA was 50 ng/ml total. Thus, although several attempts at detecting THCA in oral fluid have been made, none have successfully done so in a reliable and repeatable manner.

BRIEF SUMMARY OF THE INVENTION

An object of the present invention is to provide a drug detection method.

It is another object of the present invention to provide a drug test that is reliable, accurate, repeatable, and substantially eliminates the chance of false positive and/or false negatives.

Still another object of the present invention is to provide a novel oral fluid drug test.

Another object of the present invention is to provide a method of confirming the active intake of cannabinoids in marijuana.

Still another object of the present invention is to detect the presence of a $\Delta^9$-THC metabolite in the oral fluid as a confirmation of active marijuana use.

Another object of the present invention is to provide for a method for detecting the presence of THCA and/or THCA-glucuronide in the oral fluid.

Yet another object of the present invention is to provide a method whereby substantially all, and most preferably all, of the THCA-glucuronide present in the oral fluid is liberated to free THCA prior to quantification of the amount of THCA in the oral fluid.

Still another object of the present invention is to provide a method of showing that $\Delta^9$-THC is not metabolized by the oral fluid or the oral mucosa to produce THCA.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF DESCRIPTION OF THE DRAWINGS

FIG. 3 demonstrates the intra-day precision and accuracy of the method of the present invention over a period of five days.

DETAILED DESCRIPTION OF PREFERRED EMBODIMENT

Figure 1:
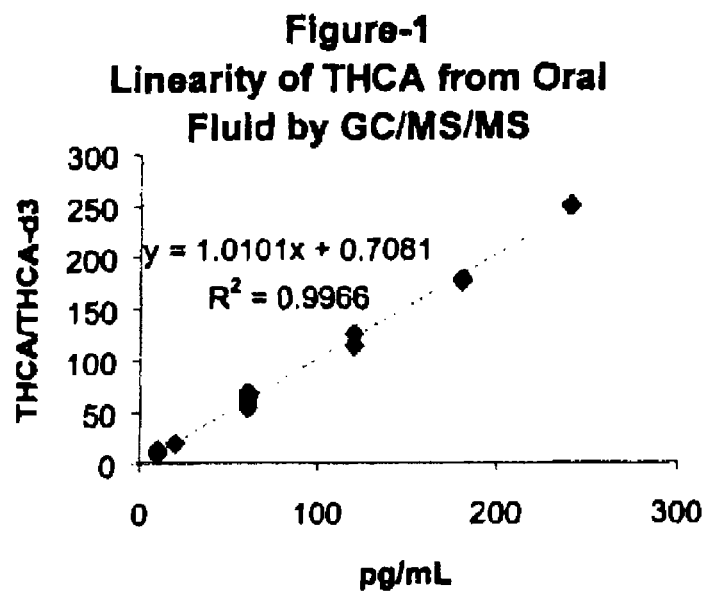
FIG. 1 shows linearity of THCA from oral fluid analyzed in accordance with the present invention using negative chemical ionization GC/MS/MS from 10 pg/mL to 240 pg/mL.

The term "oral fluid," as used herein, refers to one or more fluids found in the oral cavity individually or in combination. These include, but are not limited to, saliva and mucosal transudate. It is recognized that oral fluid can comprise a combination of fluids from a number of sources (e.g., parotid, submandibular, sublingual, accessory glands, gingival mucosa, and buccal mucosa) and the term oral fluid includes the fluids from each of these sources individually, or in combination.

The term "mucosal transudate," as used herein, refers to fluid produced by the passive diffusion of serum components from oral mucosal interstitia into the oral cavity and often forms one component of oral fluid.

The term "test subject," as used herein, is the individual to be tested for the active intake of marijuana by the method of the present invention, and is preferably a human.

The term "saliva," as used herein, refers to a combination of oral fluids secreted by the salivary glands, such as is typically found in the mouth, in particular after chewing.

The present invention is directed to a method of confirming the active intake of marijuana in a test subject by quantifying the amount of conjugated and unconjugated THCA in a sample of oral fluid from the test subject. Preferably, the amount of THCA in the oral fluid from the test subject is compared to that of a control subject. It is theorized that THCA or THCA-glucuronide will not appear in oral fluid from passive absorption of *cannabis* smoke to the oral cavity. Moreover, the present invention shows that these metabolic compounds are not a result of oral mucosal metabolism of $\Delta^9$-THC and cannot be accounted for in any other manner other than liver metabolism of $\Delta^9$-THC. See also Wall & Perez-Reyes, *The metabolism of delta9-tetrahyrocannabinol and related cannabinoids in man.*, Clin. Pharmacol., Vol. 21, at pp. 178S-189S (August-September 1981); Watanabe et al., *A cytochrome P450 isozyme having aldehyde oxygenase activity plays a major role in metabolizing cannabinoids by mouse hepatic microsomes.*, Biochem. Pharmacol., Vol. 46, No, 3, at pp. 405-11 (August 1993). Thus, in the present invention, the detection of THCA in the oral fluid serves as a biomarker useful for determination of intentional *cannabis* use.

As with urine, the cutoff concentration of THCA in the oral fluid is preferably set to minimize false positive results. The present invention uses a cutoff of about 5 pg/ml to 30 pg/ml and most preferably about 10 pg/ml to about 20 pg/ml for oral fluid testing. Typically, the cutoff is set at about 10 pg/ml or 15 pg/ml. Even at this low level, a large number of oral fluid samples can be tested with relative high-throughput, excellent reliability, and repeatability.

Of course, while it is contemplated that the detection method of the present invention may be used as the sole method for confirming the active intake of marijuana, those skilled in the art will appreciate that the present invention may be used in combination with other suitable screening methods for detecting the active intake of marijuana, such as urine, hair, blood, or other screening methods. Such complementary methods may detect $\Delta^9$-THC or its metabolites.

In the present invention, an oral fluid sample from a test subject is first obtained using conventional collection techniques. For example, the oral fluid sample may be collected by having the test subject expectorate into a cup or tube or by having the test subject place an absorbent pad in the mouth. The oral fluid sample may then be stored for a period of time prior to testing by freezing and/or using conventional buffers, preservatives, and the like. A test sample of oral fluid containing THCA (and/or the glucuronide conjugate) is then extracted from the collection device. For example, when using an absorbent pad as collection device, centrifugation and/or solvents may be used to extract the THCA (and/or glucoronide conjugate) from the absorbent pad. Next, substantially all of the conjugated THCA-glucuronide in the test sample is preferably liberated from the test sample by exposing it to alkaline conditions. The test sample containing the free THCA is then preferably purified and concentrated. Following GC, the test sample is analyzed using an MS device capable of detecting THCA in the picogram per milliliter range. Generally, the amount of THCA detected ranges from about 10 pg/ml to about 240 pg/ml, and is usually less than about 120 pg/ml.

1. Sample Collection

Oral fluid containing the test metabolite of $\Delta^9$-THC may be collected from a test subject by any of a number of collection techniques and devices well known to those of skill in the art. For example, oral fluid may be collected by having the test subject expectorate into a cup or tube. In addition, some commercially available techniques for collection involve the use of capillary tubes, suction into micropipettes, or aspiration into polypropylene syringes. The most preferred collection method involves collecting the oral fluid in the test subject's mouth by direct absorption onto a collection pad comprised of a sponge, a flexible wad of osmotic membrane, or another absorptive material such as cotton, nylon, or polyester material. Preferably, the collection pad is a thick, absorbent cotton roll or paper, such as that commonly used in dental procedures. An example of such a pad is a 1.5 inch No. 2 medium cotton roll distributed by Patterson Dental Co. (Minneapolis Minn.). Another example of a thick, absorbent cotton paper is product #300 manufactured by Schleicher and Schuell (Keene, N.H.). Typically, the collection pad is attached to a pad holder for ease of collection.

Typically, the oral fluid sample is collected according to the instructions provided with the particular collection means or device used. For example, when an absorbent collection pad is used, the collection pad is usually held against the gum and cheek until the pad absorbs a suitable amount of oral fluid. Usually, this involves contact with the gum and cheek for about two minutes. In most instances, the contact can be maintained up to about five minutes. In other instances, it may be desirable that the oral fluid sample be collected by rubbing the collection pad back and forth between the gums and cheek for about ten seconds and then holding the collection pad in position for about two minutes to about five minutes. After absorption, the oral fluid sample can be separated from the collection pad by centrifugation or by compressing the collection pad.

A number of devices for collecting oral fluid from a test subject are commercially available. These include the ORAQUICK® ORASURE®, and INTERCEPT® Oral Collection Devices by OraSure Technologies (Bethlehem, Pa.), the OMNISAL® Saliva Collection System by Saliva Diagnostic Systems (Vancouver, Wash.), the QUANTISAL™ Collection System by Immunanalysis (Pomona, Calif.), and the ORAL-EZE® collection device formerly sold by Choice-Point (Alpharetta, Ga.). See also U.S. Pat. No. 5,022,409 entitled "Oral rinse immunoglobulin collection kit for immunoassay and method thereof"; 5,339,829 entitled "Oral collection device"; U.S. Pat. No. 5,103,836 entitled "Oral Collection Device and Ket [sic] for Immunoassay"; U.S. Pat. No. 5,234,001 entitled "Container for Immunoassay with Frangible Nipple"; U.S. Pat. No. 5,334,502 entitled "Method of Collecting, Identifying and Quantifying Saliva"; U.S. Pat. No. 5,335,673 entitled "Oral Collection Device and Method for Immunoassay"; U.S. Pat. No. 5,479,937 entitled "Oral collection device"; U.S. Pat. No. 5,506,114 entitled "Methods and Kits for Detecting the Presence or Concentration of Biological Analytes"; U.S. Pat. No. 5,573,009 entitled "Oral sample collection method"; U.S. Pat. No. 5,830,410 entitled "Oral collection device and kit; and U.S. Pat. No. 6,440,087 entitled "Oral Fluid Collection Device and Collection Method," all of which are hereby incorporated by reference in their entirety.

2. Storage of the Oral Fluid Sample

In some instances, the oral fluid sample is available for immediate testing of the test metabolite. In other instances, it must be stored and shipped off-site for analysis. In the latter case, the sample may be stored by freezing at a suitable temperature. The sample may also be stored in a suitable storage device until analysis can be performed. Various storage devices for oral fluid samples are commercially available and well known to those skilled in the art. A suitable storage device is described in U.S. Pat. No. 5,234,001, which is incorporated by reference. Typically, the oral fluid sample or collection pad containing the oral fluid sample is placed into a tube containing a preservative solution. Compounds contemplated for use in the tube as a preservative include antibacterial agents, anti-fungal agents, bacteriostatic agents, fungistatic agents, and enzyme inhibitors, such as those discussed above. As an antibacterial agent, suitable agents include chlorhexidine gluconate or thimerosal. In general, the preservatives are included in a concentration that limits microbial contamination and does not adversely effect the oral fluid sample.

The preservative solution to be used in the tube can also contain a detergent that may improve removal of test ample from the collection pad during centrifugation. TWEEN® 20 (polyoxyethylene sorbitan monooleate) is a suitable detergent. Generally, a combination comprising about 0.01% to 0.2% chlorhexidine gluconate and 0.2% to 0.7% TWEEN® 20 can be used, usually about 0.1% chlorhexidine gluconate and 0.5% TWEEN® 20.

3. Extraction of a Sample Containing THCA from the Collection Pad

When the oral fluid sample is collected by having the test subject expectorate into a cup or tube, the oral fluid sample typically is purified prior to detection of the test metabolite without additional extraction steps. In the event that a collection pad is utilized to collect the oral fluid sample, the test sample of oral fluid is extracted from the pad using a suitable extraction technique prior to purification. Such extraction techniques include, but are not limited to, squeezing and/or centrifuging the collection pad to obtain the test sample of oral fluid. Typically the test sample is removed from the pad by centrifugation for about 10 minutes at about 3000 RPMs with a centrifuge radius of approximately 10 cm.

In some instances, it may be desirable to include steps to enhance extraction of the sample from the collection pad. THCA is a hydrophobic molecule with an octanol/water partition function, which causes it to remain out of water or hydrophilic environments. The compound adheres to the surfaces of common materials, including glass and plastics. Preliminary attempts to detect spiked THCA in the oral fluid collected using an collection pad indicate that the spiked THCA may become bound to the pad so that the amount of THCA collected is low when using the extraction steps recommended by the manufacturer of the collection pad (e.g., centrifugation). Thus, by implementing suitable extraction steps prior to purification, additional THCA may be recovered.

To enhance extraction of the THCA, the collection pad is removed from the plastic support and placed in a glass screw-cap vile. Most preferably, a suitable organic or aqueous solvent is added for about 30 minutes at about 70° C. The solvent is then removed to form a dried residue. The residue is then reconstituted into methanol or other suitable solvent. The mixture is then preferably incubated at room temperature for up to about 15 minutes before purification.

As discussed below, enhanced extraction of THCA from the collection pad can be performed using suitable organic or aqueous solvents. Other materials that may improve recovery of THCA from the collection pad are not limited to such solvents, also but include aqueous amphiphilic molecules like bile salts or TWEEN®. Additionally, salting out effects can be employed to remove THCA from the collection pad using divalent cationic salts such as zinc chloride.

Examples of suitable organic solvents for enhancing extraction of THCA from the collection pad contain about 0 to 85% vol/vol hexanes, about 0 to 50% vol/vol ethyl acetate, about 0 to 5% vol/vol acetic acid, about 0 to 5% vol/vol formic acid, about 0 to 5% vol/vol trifluoroacetic acid, about 0 to 99% vol/vol dichloromethane, about 0 to 66% vol/vol chloroform, about 0 to 70% vol/vol acetonitrile, about 0 to 65% vol/vol methanol, and/or about 0 to 60% vol/vol ethanol. An preferred organic solvent comprises about 80% vol/vol hexane, about 18% vol/vol ethyl acetate, and about 2% vol/vol acetic acid.

Examples of suitable aqueous solvents for enhancing extraction of the THCA include water containing about 0 to 5% wt/vol sodium deoxycholate, or about 0 to 4% vol/vol TWEEN. The TWEEN concentration is preferably about 1%, and is prepared by adding about 1.0 ml of TWEEN to one liter of water. The sodium deoxycholate solution is prepared by adding about 10 grams of sodium deoxycholate to 1 liter of water.

4. Liberation of Conjugated THCA

After extracting the THCA with a suitable solvent, the test sample is then preferably dried and reconstituted in a suitable solvent. Most preferably, the solvent includes a base so that the test sample is exposed to alkaline conditions. The solvent is preferably a mixture of ethanol and methanol in about a 2:1 or 1:1 or 1:2 ratio. The ratio of this organic solvent to aqueous solvent (1N NaOH) is about 10% to 20% vol/vol. Most preferably, the test sample fluid is dried and then reconstituted in about 1 ml of 80% 1.0 N NaOH (wt/vol, 40 g NaOH in 1 L of water), about 10% vol/vol methanol, and about 10% vol/vol ethanol. The hydroxide causes hydrolysis of the THCA-glucuronide in the solution, provide for high binding of the divalent form of THCA to the solid phase support during purification, and open the hydrophobic portions of the solid phase for hydrophobic binding of the THCA molecule.

5. Purification and Concentration

After a test sample from the collection pad has been extracted, the sample is then preferably purified and concentrated prior to quantification of the THCA content. Any suitable purification and concentration method can be employed. For example the test sample may be subjected to alkaline conditions on a solid phase extraction column. The solid phase extraction column not only purifies the test sample, but also helps liberate any remaining conjugated THCA-glucuronide to free THCA by hydrolysis. The column conditions are preferably greater than a pH of 10 since the $pK_{a2}$ of THCA is about 9.2, and greater recovery is obtained. Alternatively, the test sample may be purified and concentrated using solid phase extraction without hydrolysis, using various commercially available solid phase extraction columns. In addition, liquid/liquid extractions can be used for recovery of hydrophobic compounds. Lastly, the extract may be exposed to an antibody specific for THCA that is conjugated to a solid phase support, and then eluted with a suitable acid. In this latter instance, cross-reactivity with $\Delta^9$-THC or its metabolites may occur. In addition, the THCA may not be sufficiently liberated from THCA-glucuronide.

An exemplary and preferred solid phase extraction process and reagents useful for purification and concentration of the test sample is set forth below.

First, about 0.1 to 2.5 ml of 1.0 N NaOH is added to CEREX® Polychrome™ solid phase extraction columns, which are described in U.S. Pat. No. 5,595,653, and which is incorporated by reference. It is contemplated that the addition of NaOH hydrolyzes all or substantially all of the THCA-glucuronide as the test sample passes through the column. It is theorized that the charge state of THCA is also changed to −2, which results in a "salting out" effect of the metabolite.

Next, about 20 to 400 µl of a test sample of oral fluid is added to a sample preparation tube. As discussed above, the test sample may be obtained by having the test subject expectorate into a collection device or use a collection pad.

Controls are added to each batch of the test samples of oral fluid to ensure linearity of recovery and an absence of false positives. Each control is placed in a separate tube. Known quantities of THCA and deuterated THCA-d3 as an internal standard reference are added to each control tube. The ratio of THCA to THCA-d3 is in the controls is used to establish an accurate estimate with a known confidence interval of the amount of THCA in the test sample. The negative controls and test samples contain no added THCA, but known amounts of THCA-d3.

After waiting a suitable time and properly mixing, the test samples and controls are passed through the columns at low speed with non-reactive gas, such as nitrogen.

The columns are then washed with a wash solution comprising a water-miscible organic solvent and a base. The wash solution helps remove sodium and other ions present in the ion-exchange resin. The base also maintains the charged state of the THCA on the solid phase support. Most preferably, the base is ammonia hydroxide (30% ACS Grade). Suitable water-miscible organic solvents include methanol, acetonitrile, ethanol, and isopropanol. Preferably, the ratio of organic solvent to base (e.g. methanol to ammonia hydroxide) is no more than about 20% since higher amounts may wash off some of the THCA. Most preferably, the wash comprises about 1.0 ml of about 85:15:1 vol/vol/vol water:methanol: ammonia hydroxide.

Next, the columns are washed with about 100 to 1000 µl of methanol. The columns are then dried for about 5 to 30 minutes with non-reactive gas. The dry time will vary depending upon the flow rate and temperature of the non-reactive gas. Typically, dry time is between about 5 and 30 minutes.

The columns are then eluted using about 3 ml of about 80:20:2 vol/vol/vol hexane:ethyl acetate:acetic acid. The eluant is evaporated to dryness at about 40° C. using a continuous stream of nitrogen. Next about 50 µl of hexafluoroisopropanol ("HFIP") and 50 µL pentafluoroproprionicanhydride ("PFAA" or "PFPA") are added. The solution is capped and heated at about 75° C. for about 15 minutes. The mixture is then dried completely with a nitrogen stream. About 50 µL toluene is added to the mix. This concentrated mixture is then injected and analyzed for the presence of THCA using a suitable detector device, such as GC/MS/MS.

6. Analysis with Mass Spectrometry

In the present invention, the presence of THCA in the oral fluid sample is detected using a suitable detection device. Most preferably, the THCA is detected using tandem gas chromatography mass spectrometry. The mass spectrometer used in accordance with the present invention can resolve molecules with small mass differences and measure the mass of ions with a high degree of accuracy in the picogram per milliliter range.

Mass spectrometry methods are well known in the art (see Burlingame et al. Anal. Chem. 70:647R-716R (1998); Kinter and Sherman, Protein Sequencing and Identification Using Tandem Mass Spectrometry Wiley-Interscience, New York (2000)). The basic processes associated with a mass spectrometry method are the generation of gas-phase ions derived from the sample, and the measurement of their mass. The movement of gas-phase ions can be precisely controlled using electromagnetic fields generated in the mass spectrometer. The movement of ions in these electromagnetic fields is proportional to the mass to charge ratio (m/z) of the ion and this forms the basis of measuring the m/z and therefore the mass of a sample. The movement of ions in these electromagnetic fields allows the ions to be contained and focused which accounts for the high sensitivity of mass spectrometry. During the course of m/z measurement, ions are transmitted with high efficiency to particle detectors that record the arrival of these ions. The quantity of ions at each m/z is demonstrated by peaks on a graph where the x axis is m/z and the y axis is relative abundance. Different mass spectrometers have different levels of resolution, that is, the ability to resolve peaks between ions closely related in mass. The resolution is defined as R=m/delta m, where m is the ion mass and "delta m" is the difference in mass between two peaks in a mass spectrum. For example, a mass spectrometer with a resolution of 1000 can resolve an ion with a m/z of 100.0 from an ion with a m/z of 100.1.

Several types of mass spectrometers are available or can be produced with various configurations. In general, a mass spectrometer has the following components: a sample inlet, an ion source, a mass analyzer, a detector, a vacuum system, and instrument-control system, and a data system.

In the present invention, the oral fluid sample preferably undergoes some type of chromatography en route to the ionization source. Most preferably, the mass spectrometer is coupled directly to a gas chromatography ("GC") device. The sample is separated into a series of components that then enter the mass spectrometer sequentially for individual analysis.

The oral fluid sample is then directed to a suitable ionization device. Most preferably, a negative chemical ionization device using ammonia as the ionization gas at a pressure of about 6500 to 7500 mTorr is used as the ion source. In negative-ion chemical ionization, the buffer gas is used to slow down the electrons in the electron beam until some of the electrons have just the right energy to be captured by the analyte molecules. The buffer gas can also help stabilize the energetic anions and reduce fragmentation.

The sample is then directed to a suitable mass analyzer. Suitable mass analyzers for use in the present invention include quadrupole mass filter, ion trap mass analyzer, and time-of-flight mass analyzer, magnetic sector, and Fourier transform ion cyclotron resonance spectrometers. Again, however, the analyzer should be capable of detecting the amount of THCA in the oral fluid in the pg/ml range, most preferably between about 10 pg/ml to about 240 pg/ml.

Quadrupole mass spectrometry utilizes a quadrupole mass filter or analyzer. This type of mass analyzer is composed of four rods arranged as two sets of two electrically connected rods. A combination of rf and dc voltages are applied to each pair of rods which produces fields that cause an oscillating movement of the ions as they move from the beginning of the mass filter to the end. The result of these fields is the production of a high-pass mass filter in one pair of rods and a low-pass filter in the other pair of rods. Overlap between the high-pass and low-pass filter leaves a defined m/z that can pass both filters and traverse the length of the quadrupole. This m/z is selected and remains stable in the quadrupole mass filter while all other m/z have unstable trajectories and do not remain in the mass filter. A mass spectrum results by ramping the applied fields such that an increasing m/z is selected to pass through the mass filter and reach the detector. In addition, quadrupoles can also be set up to contain and transmit ions of all m/z by applying a rf-only field. This allows quadrupoles to function as a lens or focusing system in regions of the mass spectrometer where ion transmission is needed without mass filtering. This will be of use in tandem mass spectrometry as described further below.

Ion trap mass spectrometry utilizes an ion trap mass analyzer. In these mass analyzers, fields are applied so that ions of all m/z are initially trapped and oscillate in the mass analyzer. Ions enter the ion trap from the ion source through a focusing device such as an octapole lens system. Ion trapping takes place in the trapping region before excitation and ejection through an electrode to the detector. Mass analysis is accomplished by sequentially applying voltages that increase the amplitude of the oscillations in a way that ejects ions of increasing m/z out of the trap and into the detector. In contrast to quadrupole mass spectrometry, all ions are retained in the fields of the mass analyzer except those with the selected m/z. One advantage to ion traps is that they have very high sensitivity, as long as one is careful to limit the number of ions being tapped at one time. Control of the number of ions can be accomplished by varying the time over which ions are injected into the trap. The mass resolution of ion traps is similar to that of quadrupole mass filters, although ion traps do have low m/z limitations.

Time-of-flight ("TOF") mass spectrometry utilizes a time-of-flight mass analyzer. For this method of m/z analysis, an ion is first given a fixed amount of kinetic energy by acceleration in an electric field (generated by high voltage). Following acceleration, the ion enters a field-free or "drift" region where it travels at a velocity that is inversely proportional to its m/z. Therefore, ions with low m/z travel more rapidly than ions with high m/z. The time required for ions to travel the length of the field-free region is measured and used to calculate the m/z of the ion.

Magnetic sectors bend the trajectories of ions into circular paths of radii that depend on the momentum-to-charge ratios of the ions. Ions of larger m/z follow larger radius paths than ions of smaller m/z values so ions of differing m/z values are dispersed in space. By changing the ion trajectories through variations of the magnetic field strength, ions of different nominal mass-to-charge ratios can be focused on a detector In an Fourier transform spectrometer, ions are trapped electrostatically within a cubic cell in a constant magnetic field. A covalent orbital ("cyclotron") motion is induced by the application of a radio-frequency pulse between the excite plates. The orbiting ions generate a faint signal in the detect plates of the cell. The frequency of the signal from each ion is equal to its orbital frequency, which in turn is inversely related to its m/z value. The signal intensity of each frequency is proportional to the number of ions having that m/z value. The signal is amplified and all the frequency components are determined, yielding the mass spectrum. If the pressure in the cell is very low, the ion orbital motion can be maintained over many cycles and the frequency can be measured with very high precision. The FT-ICR instrument can therefore be used to generate very high resolution spectra.

Different mass spectrometry methods, for example, quadrupole mass spectrometry, ion trap mass spectrometry, time-of-flight mass spectrometry and tandem mass spectrometry, as described herein, can utilize various combinations of ion sources and mass analyzers which allows for flexibility in designing customized detection protocols. In addition, mass spectrometers can be programmed to transmit all ions from the ion source into the mass spectrometer either sequentially or at the same time. Furthermore, a mass spectrometer can be programmed to select ions of a particular mass for transmission into the mass spectrometer while blocking other ions. The ability to precisely control the movement of ions in a mass spectrometer allows for greater options in detection protocols which can be advantageous when a large number of tag reporters, for example, from a multiplex experiment, are being analyzed. In the present invention, the THCA is preferably detected from the oral fluid using tandem mass spectrometry (e.g., MS/MS, MS/MS/MS) that can detect THCA in the pg/ml range.

Tandem mass spectrometry can utilize combinations of the mass analyzers described above. For example, a tandem quadrupole mass spectrometer system can have a first quadrupole mass filter, followed by a collision cell, followed by a second quadrupole mass filter and then the detector. Another arrangement is to use a quadrupole mass filter for the first mass analyzer and a time-of-flight mass analyzer for the second mass analyzer with a collision cell separating the two mass analyzers. Other tandem systems are known in the art including reflectron-time-of-flight, tandem sector and sector-quadrupole mass spectrometry. In general, tandem mass spectrometers can use a first mass analyzer to separate ions according to their m/z in order to isolate an ion of interest for further analysis. The isolated ion of interest is then broken into fragment ions (called collisionally activated dissociation or collisionally induced dissociation) and the fragment ions are analyzed by the second mass analyzer. These types of tandem mass spectrometer systems are called tandem in space systems because the two mass analyzers are separated in space, usually by a collision cell. Tandem mass spectrometer systems also include tandem in time systems where one mass analyzer is used, however, the mass analyzer is used sequentially to isolate an ion, induce fragmentation, and then perform mass analysis.

Several types of tandem mass spectrometry experiments can be performed by controlling the ions that are selected in each stage of the experiment. The different types of experiments utilize different modes of operation, sometimes called "scans," of the mass analyzers. In a first example, called a mass spectrum scan, the first mass analyzer and the collision cell transmit all ions for mass analysis into the second mass analyzer. In a second example, called a product ion scan, the ions of interest are mass-selected in the first mass analyzer and then fragmented in the collision cell. The ions formed are then mass analyzed by scanning the second mass analyzer. In a third example, called a precursor ion scan, the first mass analyzer is scanned to sequentially transmit the mass analyzed ions into the collision cell for fragmentation. The second mass analyzer mass-selects the product ion of interest for transmission to the detector. Therefore, the detector signal is the result of all precursor ions that can be fragmented into a common product ion. Other experimental formats include neutral loss scans where a constant mass difference is accounted for in the mass scans.

Mass spectrometers in the tandem in time category have one mass analyzer that performs different functions at different times. For example, an ion trap mass spectrometer can be used to trap ions of all m/z. A series of rf scan functions are applied that ejects ions of all m/z from the trap except the m/z of ions of interest. After the m/z of interest has been isolated, an rf pulse is applied to produce collisions with gas molecules in the trap to induce fragmentation of the ions. Then the m/z values of the fragmented ions are measured by the mass analyzer. Ion cyclotron resonance instruments, also known as Fourier transform mass spectrometers, are an example of tandem-in-time systems.

The following examples further illustrate the present invention in detail but are not to be construed to limit the scope thereof.

EXAMPLES

Example 1

Detection of THCA in Oral Fluid

Oral fluid samples from 223 test subjects were collected with a commercially available INTERCEPT® oral fluid collection device manufactured by OraSure Technologies, Inc. (Bethlehem, Pa.) in accordance with the manufacturer's instructions. This device comprises an absorbent collection pad (e.g., cotton or a sponge) affixed to the end of a handle. The collection pad of the collection device is placed in the mouth of the subject until the collection pad is substantially saturated with oral fluid, which typically takes about four minutes.

The oral fluid samples were obtained from two drug testing facilities. The samples were divided into three groups: negative screens (A), positive screens (B), and positive confirms (C). Group A consisted of 144 oral fluid samples that had been tested by ELISA for the parent compound $\Delta^9$-THC and were negative for this test (cutoff 4.0 ng/ml $\Delta^9$-THC, cross reactive with THCA at 0.33 ng/ml, no confirmation with GC/MS/MS performed). Group B consisted of 53 oral fluid samples that screened positive by ELISA but failed to confirm using a GC/MS/MS method for the parent compound $\Delta^9$-THC (cutoff 1.0 ng/ml $\Delta^9$-THC). Finally, Group C consisted of 26 oral fluid samples that screened positive by ELISA for the parent compound $\Delta^9$-THC and were also confirmed positive for $\Delta^9$-THC by GC/MS/MS. Each of these samples from Group A, B, and C was then tested for the presence or absence of THCA by GC/MS/MS in accordance with the present invention.

Standards and controls were prepared in ethanol, and then diluted for testing into buffered saline. THCA obtained from Cerilliant (Round Rock, Tex.) at 1.0 mg/ml was diluted from two different lot numbers of stock solution. The internal standard used for this study was THCA-d3 (Cerilliant). Each standard material was independently verified to be greater than 99.9% pure by GC/MS or GC/MS/MS and to establish ion ratios expected for the material in question. 1,1,1,3,3,3-Hexafluoro-2-propanol ("HFIP") was purchased from Alfa Aesar (Ward Hill, Mass.) and used without further purification. Pentafluoropropionic anhydride ("PFAA"), purchased from Pierce (Rockford, Ill.) was also used without further purification.

Blank oral fluid from drug-free volunteers was collected, pooled, and used as negative control. This negative oral fluid was certified free from $\Delta^9$-THC by ELISA (50 ng/ml) and free from THCA (10 pg/ml) by GC/MS/MS.

The oral fluid was extracted from the INTERCEPT® oral fluid collection device by centrifugation. Typically, the test sample is removed from the pad by centrifugation for about 10 minutes at about 3000 RPMs with a centrifuge radius of approximately 10 cm. Purification and concentration of the sample was then performed before analytical determination. This was achieved using a process with reagent mixtures as follows:

Add about 0.1-2.5 ml 1.0 N NaOH to the CEREX® Polychrome™ tubes.

Add about 40-800 µL of a test sample of oral fluid.

Add controls for THCA to the tubes for calibrator, low, high, and negative.

Add the internal standard in an organic solvent to each tube and mix.

Pass the liquid through the tubes at a low speed with a non-reactive gas.

Wash with about 1.0 ml of about 85:15:1 water:MeOH:$NH_4$ on low.

Wash with methanol.

Dry columns with a non-reactive gas.

Elute using about 80:20:2 hexane:ethyl acetate:acetic acid.

Evaporate to dryness.

Add about 50 µL HFIP, about 50 µL PFAA, cap and heat at about 75° C. for about 15 minutes.

Dry completely with nitrogen, add toluene, reconstitute, and analyze.

Analysis was then performed on a GC/MS/MS consisting of a capillary gas chromatograph, whose column was directly coupled to a triple quadrupole mass spectrometer, which was operated with negative chemical ionization in daughter ion monitoring mode under computer control.

The detection device consisted of a Finnigan TSQ-7000 triple quadrupole mass spectrometer coupled with a ThermoFinnigan Trace GC and a Leap Technologies CTC A200S auto-sampler. The detection conditions were as follows:

Negative chemical ionization

Carrier gas: High purity helium at 0.7-1.0 ml/min

Reagent gas: Ammonia at 6200-7200 mTorr

CID gas: Argon at 0.65-1.25 mTorr

Injection: Split/splitless

GC column: J&W DB-5, 15 m×0.25 mm ID, 1.0 µm film thickness, or a similar fused silica column Injector temperature; 230° C.-275° C.

Column temperature: May be varied, depending on the specific column being used. Typically, a program from 130° C. to 300° C. is used in a time of 5-6 minutes.

Transfer line temperature 270° C.-300° C.

Manifold pressure: Less than $2.0 \times 10^{-5}$ Torr

Manifold temperature: 50° C.-80° C.

Electron multiplier voltage is greater than 2900

Injection needle washing program with at least five rinse steps

Injection volume of 3 µL and 0.5 µL overdraw

Retention times of each peak in the ion current profile from submitted specimens remained within +/−2% of the retention time for the calibration standard used for quantitation of the sample. Retention times varied from run to run as the column was trimmed or the instrument was serviced. The ions monitored are listed below:

| Ions Monitored for Each Analyte | | |
|---|---|---|
| Analyte | Parent Ion | Product/Daughter Ions |
| THCA | 620.5 | 492, 383 |
| THCA-$d_3$ | 623.5 | 495, 386 |

Quantitation was performed using the internal standard area of the 495-peak ratio with the 492-peak. It will be appreciated to those skilled in the art that other acceptable ions may be used. Calculation of the concentration of THCA was based on comparison of the ratio of the peak area for the prominent daughter ion 495 m/z of deuterated THCA, to the corresponding ratio of peak area for the calibration standard for the batch or sequence of injections. These calculations were performed using the Finnigan Excaliber software program and with the use of Microsoft Excel for ion ratio calculations of the qualification ion peak chosen.

As shown in FIG. 1, the linearity of response was determined from 10 pg/ml to 240 pg/ml. In addition, a Pearson's correlation coefficient was calculated in this range, and typically exceeded 0.995. Each sample for this test was equally weighted and the line was not forced through the origin. Multiple determinations of the ratio of THCA/THCA-d3 at each concentration was used for this calculation.

Figure 2:
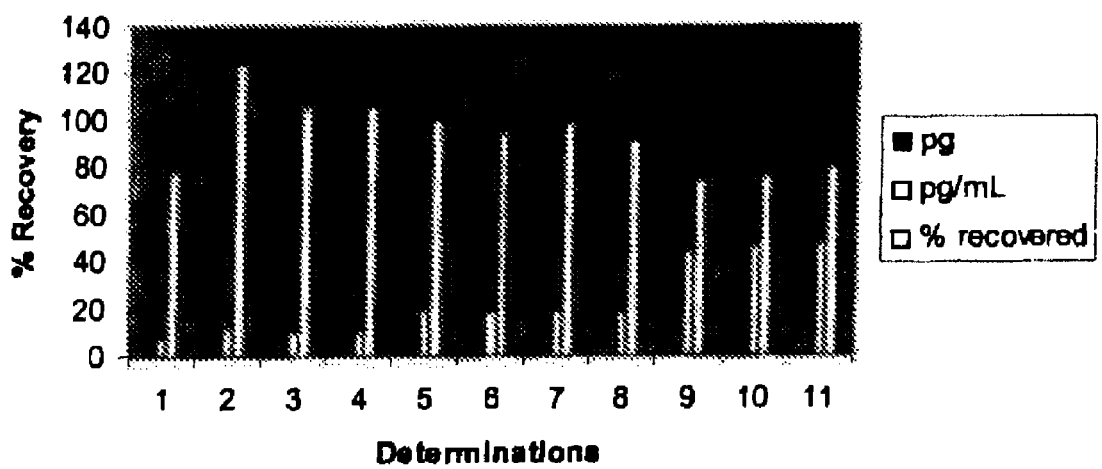
FIG. 2 shows the recovery of THCA from spiked oral fluid at three concentrations: 10 pg/mL, 20 pg/mL, and 60 pg/mL. Recovery variation at these levels was 21%, 4%, and 7% respectively.

The absolute recovery was also determined. The internal standard was added following solid phase extraction and the ratio of peak intensities for the ion of interest was compared to extracted controls. The absolute recovery was expressed in terms of a percentage of recovered THCA/THCA-d3. Three samples at three different concentrations were measured: 10 pg/ml, 20 pg/ml, and 60 pg/ml. As shown in FIG. 2 and Table 1, the present invention achieved high recoveries near 100%. The average recovery at 10 pg/mL using only 100 µL was about 104%. Moreover, precision and accuracy were excellent at these levels. For example, precision at 20 pg/mL was about 4%.

TABLE 1

Recovery of THCA from Spiked Oral Fluid

| pg | pg/ml | % recovered | Target (pg/ml) | average | % RSD |
|---|---|---|---|---|---|
| 0.78 | 7.8 | 78 | 10 | | |
| 1.24 | 12.4 | 124 | 10 | | |
| 1.06 | 10.6 | 106 | 10 | | |
| 1.06 | 10.6 | 106 | 10 | 103.50 | 19.00 |
| 2 | 20 | 100 | 20 | | |
| 1.9 | 19 | 95 | 20 | | |
| 1.98 | 19.8 | 99 | 20 | | |
| 1.82 | 18.2 | 91 | 20 | 96.25 | 4.11 |
| 4.44 | 44.4 | 74 | 60 | | |
| 4.58 | 45.8 | 76.3 | 60 | | |
| 4.8 | 48 | 80 | 60 | 76.78 | 3.02 |

The accuracy and precision of measurement was also determined. Accuracy, expressed as a percentage of sample concentration relative to expected concentration, was performed at the same three concentrations used for absolute recovery determination. Precision at these same three concentrations was performed on five separate days. The percent relative standard deviation (% RSD) was calculated. The results are set forth in Table 2 below and in FIG. 3.

TABLE 2

Intra-day Precision and Accuracy

| Day | low | cal | high |
|---|---|---|---|
| 1 | 9.3 | 20.0 | 56.7 |
| 2 | 14.0 | 18.5 | 63.7 |
| 3 | 12.8 | 20.1 | 63.3 |
| 4 | 10.7 | 24.9 | 49.8 |
| 5 | 11.8 | 20.8 | 67.6 |
| Average | 11.7 | 20.9 | 60.2 |
| stdev | 2.4 | 0.9 | 3.9 |
| % RSD | 20.8 | 4.2 | 6.6 |

| | Accuracy | Precision |
|---|---|---|
| Low | 117 | 21% |
| Cal | 104 | 4% |
| High | 100 | 7% |

As discussed more fully below, this example illustrates how the detection of THCA in oral fluids can be used as a method of detecting marijuana use. The method combines an extraction procedure based on anion exchange coupled with a highly sensitive negative chemical ionization GC/MS/MS method for quantitation and forensic determination of THCA. The method also detects free THCA and liberates the glucuronidated THCA.

As set forth in more detail below, the frequency distribution of positive results for THCA from groups A, B, and C were 1.4%, 9.9%, and 88% respectively. Even though the sample population for these groups was relatively small, several statistical inferences can be made based on these numbers. In general, the data indicates that a cutoff of about 10 pg/ml of THCA in the present invention correlates well with $\Delta^9$-THC detection in the oral fluid.

Of the 144 test subjects tested from Group A (screened negative for $\Delta^9$-THC by ELISA), two had THCA levels above 10 pg/ml. Thus, the samples that screened negative by ELISA had detectable levels of THCA present at a frequency of about 1%.

Of the 53 test subjects tested from Group B (screened positive by ELISA for $\Delta^9$-THC but not confirmed by GC/MS/MS analysis), five had THCA levels above 10 pg/ml. Thus, the group that screened positive and failed to confirm (Group B) tested positive for THCA above 10 pg/ml at a rate of about 10%.

Finally, of the 26 samples that were screened and confirmed as positive for $\Delta^9$-THC (Group C), nearly 100% of the test subjects had detectable levels of THCA. While some samples contained detectable levels of THCA below 10 pg/ml, the limit of reliable quantitation in the example from a statistical standpoint was set at about 10 pg/ml. Twenty-three (23) samples or about 88% had THCA levels above 10 pg/ml. Samples in this group also had levels of THCA as high as 142 pg/ml.

Importantly, THCA was detected in the samples even though the samples were obtained after long-term storage at two separate drug-testing companies. Some of the samples were in storage for extended lengths of time, up to several years. Because even short-term storage (e.g., weeks) may have recovery reducing effects of THCA from oral fluid, it is contemplated that the results may improve if the oral fluid samples are tested more contemporaneously with collection.

Example 2

THCA-Glucuronide Liberation

THCA-glucuronide was used to determine if THCA was quantitatively liberated when extracted using the alkaline extraction procedures described herein. THCA-glucuronide was purchased (Alltech Applied Science, State College, Pa.), and determined to be greater than 99% pure when assayed for THCA by GC/MS/MS. This material was subjected to alkaline hydrolysis with NaOH and extracted using the extraction method discussed herein and quantitated as THCA. A theoretical percent recovery was used to measure the amount of THCA recovered in moles compared to the label claim of the standard material.

As shown in Table 3, THCA recovery from THCA-glucuronide spiked oral fluid was about 95% of the theoretical spiked amount. This was repeated in triplicate using THCA at 60 pg/mL equivalent for the molar ratio of the glucuronidated THCA. The data shows that the glucuronidated THCA, when present, is likely completely released as free THCA. Thus, if the glucuronide metabolite is present in the oral fluid of the test subjects in Example 1, it was likely measured and reported as free THCA.

TABLE 3

THCA-glucuronide spiked at 66 pg/mL equivalent THCA

| n = 3 | Recovered THCA (pg/mL) |
|---|---|
| 1 | 64.47 |
| 2 | 70.80 |
| 3 | 52.65 |
| Average | 62.64 |
| % Recovery | 94.91 |

Example 3

Confirmation of No Detectable THC Metabolism by Oral Fluid

In this example, $\Delta^9$-THC metabolism in oral fluid was investigated. $\Delta^9$-THC was incubated at about 37° C. in oral fluid for several hours. THCA levels were assayed versus time to ensure metabolism of $\Delta^9$-THC to THCA or THCA-glucuronide in the oral cavity or mucosa was not a possible source of the measured result. This was performed in triplicate at 10 ng/ml using certified negative oral fluid samples. $\Delta^9$-THC standard material of known purity was used.

$\Delta^9$-THC metabolism to THCA was not detected during this experiment. Further, it has been reported that $\Delta^9$-THC metabolism occurs in the liver. See Watanabe, et al., *A cytochrome P450 isozyme having aldehyde oxygenase activity plays a major role in metabolizing cannabinoids by mouse hepatic microsomes*, Biochem Pharmacol., Vol. 46 No. 3, at pp. 405-11 (August 1993). Thus, these results confirm that it is very unlikely that the oral mucosa has the metabolic capacity to convert $\Delta^9$-THC to THCA or THCA-glucuronide.

From the foregoing, it will be seen that this invention is one well adapted to attain all ends and objectives herein-above set forth, together with the other advantages which are obvious and which are inherent to the invention. In addition, while specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed is:

1. A method for quantifying the amount of 11-nor-$\Delta^9$-THC carboxylic acid ("THCA") in a sample comprising the steps of:
   providing a sample suspected of containing THCA;
   treating said sample with pentafluoropropionic anhydride;
   ionizing treated THCA from the sample under conditions suitable to produce one or more ions detectable by mass spectrometry, wherein said one or more ions comprises a parent ion with a mass to charge ratio (m/z) of 620.5;
   determining the amount of said one or more ions by tandem mass spectrometry; and
   using the amount of said one or more ions to determine the amount of THCA in the sample.

2. The method of claim 1, further comprising subjecting the treated THCA to gas chromatography (GC) prior to ionization.

3. The method of claim 1, wherein said ionizing comprises negative chemical ionization.

4. The method of claim 1, wherein said one or more ions detectable by tandem mass spectrometry further comprise one or more fragment ions selected from the group of ions with mass to charge ratio (m/z) of 492 and 383.

5. The method of claim 1, further comprising purifying THCA in the sample by solid phase extraction to generate a purified sample prior to treating with pentafluoropropionic anhydride.

6. The method of claim 5, wherein said one or more ions detectable by tandem mass spectrometry further comprise one or more fragment ions selected from the group of ions with mass to charge ratio (m/z) of 492 and 383.

7. The method of claim 1, wherein the amount of THCA detected in said sample is less than about 240 pg/ml.

8. The method of claim 1, wherein said sample is an oral fluid sample.

9. The method of claim 8, wherein said oral fluid sample is obtained from a test subject using a collection pad which is placed in the oral cavity of said test subject.

10. The method of claim 9, wherein said pad is impregnated with one or more of a preservative, protein binding blocking agent, or detergent.

11. The method of claim 9, further comprising the step of storing the oral fluid sample in a preservative solution prior to said treating step.

12. The method of claim 9, further comprising the step of extracting THCA and/or THCA-glucuronide from the collection pad using one or more organic reagents.

13. The method of claim 9, further comprising the step of extracting THCA and/or THCA-glucuronide from the pad using an aqueous reagent mixture.

14. The method of claim 8, further comprising purifying THCA in the sample by solid phase extraction to generate a purified sample prior to treating with pentafluoropropionic anhydride.

* * * * *